United States Patent [19]

Robinson et al.

[11] Patent Number: 4,532,206

[45] Date of Patent: Jul. 30, 1985

[54] β-STREPTOCOCCUS SELECTIVE MEDIUM

[75] Inventors: John M. Robinson, Tuscaloosa, Ala.; Gregory D. Rodgers, Ellisville, Mo.

[73] Assignee: Vitek Systems, Inc., Hazelwood, Mo.

[21] Appl. No.: 399,782

[22] Filed: Jul. 19, 1982

[51] Int. Cl.³ .................... C12Q 1/29; C12Q 1/04; C12Q 1/14; C12N 1/20
[52] U.S. Cl. .................... 435/36; 435/29; 435/34; 435/253; 435/885
[58] Field of Search .......... 435/102, 29, 30, 34, 435/36, 244, 253, 810, 800, 885

[56] References Cited

U.S. PATENT DOCUMENTS

| 3,699,003 | 7/1970 | Kronish et al. | 435/36 |
|---|---|---|---|
| 3,781,192 | 12/1973 | Wood et al. | 435/36 |
| 3,790,447 | 2/1974 | Hirata et al. | 435/36 |
| 4,035,238 | 7/1977 | Meyer et al. | 435/6 |
| 4,259,442 | 3/1981 | Gayral | 435/36 |
| 4,288,543 | 9/1981 | Sielaff et al. | 435/37 |
| 4,312,942 | 1/1982 | Blobel et al. | 435/13 |

FOREIGN PATENT DOCUMENTS 2717981 11/1977 Fed. Rep. of Germany ........ 435/36

OTHER PUBLICATIONS

Lehninger, A. L. *Biochemistry*, Worth Publishers, Inc., New York, pp. 288–289 (1982).
Crowley, N. et al., *J. Gen. Microbiol.* vol. 13, pp. 226–234 (1955), "The Formation of a Starch–Like Polysaccharide from Maltose by Strains of *Streptococcus pyogenes*".
Crowley, N., *J. Gen. Microbiol.*, vol. 13, pp. 218–225 (1955), "The Action of Streptococcal Amylose in Relation to the Synthesis of an Amylosaccharide by Amylolytic Strains of *Streptococcus pyogenes*".
*Manual of Clinical Microbiology*, 3rd Edition, Lennette, E. H. et al., editors, Chapter 8, "Streptococci and Aerococci", by Facklam, R. R., Amer. Soc. for Microbiol., Washington, D.C. pp. 88–110, (1980).
*Microbial Polysaccharides and Polysaccharases*, Berkeley et al., Editors, Chapter 4, "Pullulan Synthesis by *Aureobasidium pullulans*", by Catley, B. J., Academic Press, New York, pp. 69–84, 298 (1979).
*Chemical Abstracts*, vol. 97, p. 359, Abstract No. 123588h, Davis et al., "Polysaccharase Activity in *Streptococcus agalactiae* (Group B Streptococci)", (1982).
*Hackh's Chemical Dictionary*, 4th Edition, Grant, J., Consultant, McGraw-Hill, New York, pp. 47–48 and 670–671 (1969).
Crowley, N., *J. Gen. Microbiol.*, vol. 4, pp. 156–170 (1949), "The Degradation of Starch by Strains of Group A Streptococci Having Related Antigens".
Crowley, N., *J. Gen. Microbiol.*, vol. 10, pp. 411–426 (1954), "On Amylolytic Strains of *Streptococcus pyogenes*".

Primary Examiner—Thomas G. Wiseman
Assistant Examiner—Jayme A. Huleatt
Attorney, Agent, or Firm—Max Geldin

[57] ABSTRACT

A liquid β-streptococcus selective medium for the growth and detection of β-hemolytic streptococci without allowing the growth of enterococci and other non-β-hemolytic streptococci, consisting essentially of 0.2–0.4 gm. pullulan as carbohydrate source based on 93–72 ml water, a protein source such as a combination of Proteose Peptone #3, (a dried meat digest) and Biosate (pancreatic digest of casein combined with yeast autolysate), an inhibitor of the growth of Pseudomonas, such as thallous acetate, an inhibitor of the growth of gram negative organisms other than Pseudomonas, such as nalidixic acid, an inhibitor of the growth of staphylococci such as Gentamycin, and reduced aniline blue indicator.

7 Claims, No Drawings

β-STREPTOCOCCUS SELECTIVE MEDIUM

CROSS REFERENCES TO RELATED PATENTS

The present invention can be used with the optical detection systems disclosed in U.S. Pat. No. 3,963,355, entitled, "Process and Apparatus for Analyzing Specimens for the Presence of Microorganisms Therein"; U.S. Pat. No. 4,118,280 entitled, "Automated Microbial Analyzer"; U.S. Pat. No. 4,116,775 entitled, "Machine and Process for Reading Cards Containing Medical Specimens"; and U.S. Pat. No. 4,062,876 entitled, "Sensitive PH Indicator". The information therein is incorporated by reference as though fully set forth herein below.

BACKGROUND OF THE INVENTION

The patents referenced above describe mechanisms and apparatus suitable for analyzing speciments for specific microorganisms utilizing a plastic tray or card which contains a plurality of dried culture media specific to a single genus or species of organism. The dried media are contained in separate cells in the card which are connected by a network of passageways to a filling port. When a fluid sample is inserted into the card, mixed with media in the cells, and incubated, the organisms present in the specimen interact with the specific culture media. The interaction of the specimen and the specific culture media produces characteristic optical changes in the contents of the cell which are read to indicate presence of the organisms. The optical change in each cell involves a change in light transmitting properties thereof either through a color change or a change in turbidity. The optical change usually is caused by the metabolic activity of the organism which, for example, may produce an acid which changes the color of a pH sensitive indicator in the media. The change in the light transmitting properties of the medium also can be caused by a precipitate forming in the medium due to metabolic activity of the organism or by the mass of growing colonies of the organism. The metabolically caused changes generally yield considerably earlier results than do growth caused changes. The specific media designed for use in the cards of the aforesaid system all are designed to favor growth of one genus or species of microorganism and to inhibit growth of other organisms. The media are capable of being dried and they are formulated to function in the low oxygen environment of the card described in detail in the above referenced patents.

There are several media commercially available for the isolation of streptococci. These media support the growth of all streptococci, including the group D enterococci and other non-β-hemolytic streptococci.

Currently, the medium of choice for the detection of β-hemolytic streptococci is blood agar. This medium supports the growth of most bacteria but, because of the incorporation of blood cells, the β-streptococci cause large zones of hemolysis to aid in their detection. Another medium in common use is Streptosel Broth (BBL) which is a selective broth for streptococci. Group D. Enterococci grow well on this medium as well as some strains of staphylococci. Pikes medium and Columbia Broth are commonly used also, but for separation of streptococci in these media, blood cells must be incorporated.

It is accordingly an object of the present invention to provide a novel β-streptococcus selective medium for the growth and detection of β-hemolytic streptococci only, without allowing the growth of enterococci and the other non-β-hemolytic streptococci, in a relatively short period.

Another object of the invention is the provision of a selective medium of the above type without requiring the incorporation of blood cells.

A still further object is to provide a selective medium of the above type which does not permit the growth of non-β-hemolytic streptococci whether present individually or in combination with β-hemolytic streptococci.

SUMMARY OF THE INVENTION

The above objects and advantages of the present invention for the growth of β-hemolytic streptococci only, without the growth of enterococci and the other non-β-hemolytic streptococci, is based on the concept of the incorporation of pullulan into the medium, together with other essential components, as described below. This differentiation or split is achieved by the ability of all β-hemolytic streptococci tested to produce acid from the unusual substrate pullulan. Pullulan is a commercially available carbohydrate that is used in the present invention to split out the non-β-hemolytic streptococci due to their inability to produce acid from it. Most media presently available select for the growth of the enterococci. These include SF Broth, Enterococcus Confirmatory Broth, Ethyl Violet Azide Broth, Mitis Salivarius Agar, and others.

The selective medium of the invention more specifically consists essentially of pullulan as carbohydrate, a protein or nitrogen source such as Proteose Peptone #3, an inhibitor of the growth of Pseudomonas such as thallous acetate, an inhibitor of the growth of gram negative organisms other than Pseudomonas, such as nalidixic acid, an inhibitor of the growth of staphylococci, such as Gentamycin, and reduced aniline blue indicator, in certain preferred ranges of proportions, as described in greater detail below, and water.

Other components such as sodium chloride, bovine serum albumin, vitamin $B_{12}$ and sodium thioglycollate can be added, for purposes set forth in greater detail below.

The β-streptococcus selective medium of the present invention has the advantage over other presently employed media in that, because a novel way of detecting these organisms is used, employing pullulan, blood cells are not required. This medium was designed to be used in the Auto Microbic System (AMS) of above U.S. Pat. No. 4,118,280, so that an indicator compatible with its optic system is incorporated. Using the AMS, this medium is capable of detecting β-streptococci in 10-13 hours, as compared to 18-24 hours incubation for plate media.

DETAILED DESCRIPTION OF THE INVENTION

The selective medium of the present invention consists essentially of pullulan as the carbohydrate source which selectively allows the growth of β-hemolytic streptococci without allowing the growth of enterococci and the other non-β-hemolytic streptococci. Pullulan is a viscous polysaccharide extracellularly produced by growing a fungus-like yeast, commonly called "black yeast." It is available from Sigma Chemical Company, St. Louis, Mo. This material is employed in an amount of about 1.0 to about 8.0 gm/l. All β- hemolytic streptococci have the ability to produce acid from pullulan, while the non-β-hemolytic streptococci do not have this ability.

A protein source is required for the growth of the β-streptococci organisms. Trypticase and Triptone. Acidicase, Gelysate, Lactalysate, Myosate, Neopeptone, Pantone, Phytone, Polypeptone, Proteose Peptone, Thiotone, Trypticase, and Tryptone. As protein sources, Proteose Peptone #3 from Difco and Biosate BBL, and mixtures thereof as noted in the Example below, were found to give optimal growth Proteose Peptone #3 is a trademark of Difco Laboratories, Detroit, Michigan, denoting a dried meat digest product, and Biosate is a trademark of Baltimore Biological Laboratories, denoting pancreatic digest of casein combined with yeast autolysate. The protein source can be employed in an amount of about 2.0 to about 12.0 gm/l.

The protein sources, particularly Proteose Peptone #3, and Biosate are incorporated into the medium to allow for the growth of the β-hemolytic streptococci once they have established an energy source from the carbohydrate substrate pullulan.

In addition, various components can be added to the medium to enhance the performance thereof by supplying various growth nutrients. Such growth nutrients can include sodium chloride, bovine serum albumin, and vitamin $B_{12}$. Sodium chloride can be employed in an amount of about 0.25 to about 4.0 gm/l, and the bovine serum albumin in an amount of about 50 to about 200 ml/l and vitamin $B_{12}$ in an amount of about 10.0 to about 40.0 ml/l (1% solution).

Sodium thioglycollate is a reducing agent added to reduce the oxygen tension in the medium. This addition increases the amount of acid produced by the β-streptococci. This component is employed in an amount of about 1.0 to about 6.0 gm/l.

A substance, preferably thallous acetate, is also added to the medium to inhibit the growth of Pseudomonas. This component is employed in an amount of about 0.05 to about 0.30 gm/l.

A substance, preferably nalidixic acid, is also added to inhibit the growth of gram negative organisms other than Pseudomonas, in an amount of about 0.005 to about 0.033 gm/l.

A substance which inhibits the growth of staphylococci is also incorporated, particularly, Gentamycin, e.g. as the sulfate. This component is employed in an amount of about 250 to about 4,000 μg/l.

Reduced aniline blue is employed as the acid indicator in the medium. Reduced aniline blue is produced as described in U.S. Pat. No. 4,062,876, by reducing aniline blue by the sequential addition of sodium thioglycollate. The disclosure of this patent is incorporated herein by reference. At the pH of the medium, ranging from 7.0 to 7.4, β-streptococci organisms turn the medium from a red color to blue, indicating acid production. Negative organisms cause the medium to remain red, a color not detected by the AMS instrument. Reduced aniline blue is employed in an amount of about 10 to about 40 ml/l.

Distilled water is employed in formulating the medium.

Various representative formulations of the selective medium of the invention are set forth in the table below:

TABLE

| Components | Range of Proportions |
| --- | --- |
| Pullulan | .1–.8 g |
| Proteose Peptone #3 | .2–1.2 g |
| Biosate | .2–1.2 g |
| Sodium Chloride | .025–.4 g |
| Bovine Serum Albumin (5%) | 5–20 ml |
| Vitamin $B_{12}$ (1% solution) | 1–4 ml |
| Sodium Thioglycollate | .1–.6 g |
| Thallous Acetate | .005–.03 g |
| Nalidixic Acid | 500–3000 μg |
| Gentamycin | 25–400 μg |
| Reduced Aniline Blue | 1–4 ml |
| Distilled Water | 93–72 ml |
| pH | 7.0–7.4 |

The following is an example of a specific formulation of the medium according to the invention, for use in the Automatic Microbial Analyzer of the above U.S. Pat. No. 4,118,280.

EXAMPLE

| Components | Formulation per Liter |
| --- | --- |
| Pullulan | 3.0 g |
| Proteose Peptone #3 | 3.0 g |
| Biosate | 3.0 g |
| Sodium Chloride | 1.0 g |
| Bovine Serum Albumin (5%) | 100.0 ml |
| Vitamin $B_{12}$ (1% w/v stock solution) | 20.0 ml |
| Sodium Thioglycollate | 2.5 g |
| Thallous Acetate | 0.125 g |
| Nalidixic Acid (1000 μg/ml stock solution - w/v) | 12.5 ml |
| Gentamycin Sulfate (1000 μg/ml stock solution - w/v) | 1.0 ml | w/v = weight to volume

All of the above components are dissolved in 850 ml distilled water and the pH adjusted to about 6.3. Reduced aniline blue indicator is added in an amount of 20 ml, and the pH is adjusted to a final pH of 7.2 by addition of distilled water to produce 1000 ml of solution. The medium is then sterilized using a 0.45 micron membrane filter apparatus.

As prepared, the medium of the example is used according to the invention in the cells and cards described in U.S. Pat. No. 4,118,280 entitled "Automatic Microbial Analyzer," for the detection of β-streptococci, by a change in the color of the medium from red to blue. 20 μl of the above medium is dispensed into the appropriate microcell in the AMS card and a fluid specimen is injected into the filling port of the card and the card is placed in the AMS instrument. If β-streptococci are present, the medium will change from red to blue and be detected by the instrument as a positive culture. The specimen of β-streptococci employed for analysis can be a pure culture of β-streptococci or a polymicrobic sample without affecting the results utilizing the medium of the invention.

From the foregoing, it is seen that the invention provides a novel selective medium for the growth and detection of β-hemolytic streptococci without permitting the growth of enterococci and the other non-β-hemolytic streptococci, based essentially on the use of the substrate pullulan as the carbohydrate source. The selective medium of the present invention is readily applicable for use in automatic bacterial identification systems, identifies β-streptococci in a relatively short period e.g. 10–13 hours as compared to 24 hours using conventional methods, does not require the use of blood cells as in the case of conventional media, and does not allow the growth of non-β-hemolytic streptococci.

Although the above medium of the invention was designed particularly for use in the AMS instrument noted above for identification of β-streptococci, agar can be added to the formulation to make a plate medium, which can be used in place of blood agar in the clinical laboratory to detect β-streptococci.

Since various changes and modifications of the invention will occur to those skilled in the art, the invention is not to be taken as limited except by the scope of the appended claims.

We claim:

1. In a liquid selective medium for the identification of β-hemolytic streptococci in clinical samples containing a carbohydrate, a suitable protein source and reduced aniline blue indicator, wherein the improvement comprises employing pullulan as the carbohydrate source, in an amount of about 1.0 to about 8.0 gm/l, thereby allowing the growth of β-hemolytic streptococci only, without allowing the growth of enterococci and other non-β-hemolytic streptococci.

2. A liquid β-streptococcus selective medium for the growth and detection of β-hemolytic streptococci only, without permitting the growth of enterococci and other non-β-hemolytic streptococci, comprising about 1.0 to about 8.0 gm/l pullulan, about 2.0 to about 12.0 gm/l of a protein source selected from the group consisting of (a) a dried meat digest product, (b) pancreatic digest of casein combined with yeast autolysate, and mixtures of (a) and (b), and about 10 to about 40 ml/l of reduced aniline blue indicator.

3. The liquid selective medium as defined in claim 1, including thallous acetate as inhibitor of the growth of Pseudomonas, in an amount of about 0.05 to about 0.30 gm/l, nalidixic acid as inhibitor of the growth of gram negative organisms other than Pseudomonas, in an amount of about 0.005 to about 0.03 g/l, and Gentamycin as inhibitor of the growth of staphylococci, in an amount of about 250 to about 4,000 g/l.

4. The liquid selective medium as defined in claim 3, including bovine serum albumin in an amount of about 50 to about 200 ml/l and vitamin $B_{12}$ in an amount of about 10.0 to about 40.0 ml/l.

5. A liquid β-streptococcus selective medium for the growth and detection of β-hemolytic streptococci only, without permitting the growth of enterococci and the other non-β-hemolytic streptococci, comprising the following components in the following proportions:

Pullulan: 0.1–0.8 g
Dried meat digest: 0.2–1.2 g
Pancreatic digest of casein combined with yeast autolysate: 0.2–1.2 g
Sodium Chloride: 0.025–0.4 g
Bovine Serum Albumin (5%): 5–20 ml
Vitamin $B_{12}$ (1% solution): 1–4 ml
Sodium Thioglycollate: 0.1–0.6 g
Thallous Acetate: 0.005–0.03 g
Nalidixic Acid: 500–3000 μg
Gentamycin: 25–400 μg
Reduced Aniline Blue: 1–4 ml
Distilled Water: 72–93 ml
pH 7.0–7.4.

6. In a process for the detection of β-streptococcus organisms comprising inoculating a medium with a sample; incubating the inoculated medium and monitoring the incubated medium, wherein the improvement comprises using as the medium a liquid β-streptococcus selective medium comprising about 1.0 to about 8.0 gm/l pullulan, about 2.0 to about 12.0 gm/l of a protein source selected from the group consisting of (a) a dried meat digest product, (b) pancreatic digest of casein combined with yeast autolysate, and mixtures of (a) and (b), and about 10 to about 40 ml/l of reduced aniline blue indicator, and monitoring by periodic photometric measurements or by visual examination changes in color of said incubated medium from red to blue.

7. In a process for the detection of β-streptococcus organisms comprising inoculating a medium with a sample, incubating the inoculated medium and monitoring the incubated medium, wherein the improvement comprises using as the medium a liquid β-streptococcus selective medium comprising the following components in the following proportions:

Pullulan: 0.1–0.8 g
Dried meat digest: 0.2–1.2 g
Pancreatic digest of casein combined with yeast autolysate: 2–1.2 g
Sodium Chloride: 0.025–0.4 g
Bovine Serum Albumin (5%): 5–20 ml
Vitamin $B_{12}$ (1% solution): 1–4 ml
Sodium Thioglycollate: 0.1–0.6 g
Thallous Acetate: 0.005–0.03 g
Nalidixic Acid: 500–3000 μg
Gentamycin: 25–400 μg
Reduced Aniline Blue: 1–4 ml
Distilled Water: 72–93 ml
pH 7.0–7.4, and monitoring by periodic photometric measurements or by visual examination changes in color of said medium from red to blue.

* * * * *

UNITED STATES PATENT AND TRADEMARK OFFICE
CERTIFICATE OF CORRECTION

PATENT NO.  : 4,532,206
DATED       : July 30, 1985
INVENTOR(S) : John M. Robinson and Gregory D. Rodgers It is certified that error appears in the above-identified patent and that said Letters Patent is hereby corrected as shown below:

Column 3, line 5, delete "Trypticase and Triptone."

Column 3, delete lines 6 and 7.

Column 3, line 8, delete "tone, Thiotone, Trypticase, and Tryptone."

Column 3, line 44, delete "0.033" and insert --0.03--.

Column 6, line 38, delete "2-1.2" and insert --.2-1.2--.

Signed and Sealed this

Third Day of November, 1987

Attest:

DONALD J. QUIGG

*Attesting Officer*    *Commissioner of Patents and Trademarks*